US009241922B2

(12) United States Patent
Chen et al.

(10) Patent No.: US 9,241,922 B2
(45) Date of Patent: Jan. 26, 2016

(54) PHARMACEUTICAL SOLUTION OF TAXANES COMPRISING PH REGULATOR AND PREPARATION METHOD THEREOF

(75) Inventors: Jianming Chen, Tianjin (CN); Baoan Gao, Tianjin (CN); Li Deng, Tianjin (CN); Qiuxia Yang, Tianjin (CN); Jing Sun, Tianjin (CN); Wei Liu, Tianjin (CN); Peng Gu, Tianjin (CN); Yingying Zhang, Tianjin (CN); Jialiang Zhang, Tianjin (CN)

(73) Assignee: Tasly Holding Group Co., Ltd., Tianjin (CN)

( * ) Notice: Subject to any disclaimer, the term of this patent is extended or adjusted under 35 U.S.C. 154(b) by 0 days.

(21) Appl. No.: 13/393,233

(22) PCT Filed: Oct. 22, 2010

(86) PCT No.: PCT/CN2010/077996
§ 371 (c)(1), (2), (4) Date: Feb. 29, 2012

(87) PCT Pub. No.: WO2011/047637
PCT Pub. Date: Apr. 28, 2011

(65) Prior Publication Data

US 2012/0157517 A1 Jun. 21, 2012

(30) Foreign Application Priority Data

Oct. 23, 2009 (CN) .......................... 2009 1 0070931

(51) Int. Cl.
*A61K 31/337* (2006.01)
*A61K 9/00* (2006.01)
*A61K 47/10* (2006.01)
*A61K 47/12* (2006.01)

(52) U.S. Cl.
CPC ............. *A61K 31/337* (2013.01); *A61K 9/0019* (2013.01); *A61K 47/10* (2013.01); *A61K 47/12* (2013.01)

(58) Field of Classification Search
CPC ..... A61K 9/0019; A61K 47/12; A61K 47/10; A61K 31/337
USPC .......................................................... 514/449
See application file for complete search history.

(56) References Cited

U.S. PATENT DOCUMENTS

| | | | | |
|---|---|---|---|---|
| 6,107,333 | A | 8/2000 | Andersson | |
| 6,136,846 | A * | 10/2000 | Rubinfeld et al. | 514/449 |
| 7,030,155 | B2 * | 4/2006 | Lambert et al. | 514/449 |
| 2007/0202070 | A1 * | 8/2007 | Kamachi et al. | 424/70.13 |
| 2007/0286767 | A1 * | 12/2007 | Burke et al. | 422/28 |
| 2007/0293577 | A1 * | 12/2007 | Kamachi et al. | 514/574 |
| 2008/0306137 | A1 | 12/2008 | Hao | |
| 2008/0319048 | A1 | 12/2008 | Palepu et al. | |

FOREIGN PATENT DOCUMENTS

| | | | |
|---|---|---|---|
| CN | 1228022 | | 9/1999 |
| CN | 1382038 | | 11/2002 |
| CN | 1535679 | | 10/2004 |
| CN | 101244053 | A | 8/2008 |
| CN | 101288642 | A | 10/2008 |
| EP | 1862183 | A1 | 5/2007 |
| EP | 1 862 183 | A1 * | 12/2007 |
| JP | 2008514720 | A | 5/2008 |
| WO | 9300928 | | 1/1993 |
| WO | WO 98/00128 | A1 | 1/1998 |
| WO | WO 01/30319 | A1 | 5/2001 |
| WO | 2004/043390 | A2 | 5/2004 |
| WO | 2006133510 | A1 | 12/2006 |
| WO | WO 2009002425 | A2 * | 12/2008 |
| WO | 2009047794 | A2 | 4/2009 |
| WO | 2009/087678 | A2 | 7/2009 |

OTHER PUBLICATIONS

Adams et al., Journal of National Cancer Institute Monographs No. 15:141-147 (1993).
Extended European Search Report, PCT/CNCN2010077996, 5 pages, dated Aug. 20, 2013.
Dordunoo et al. International Journal of Pharmacutics, 133:191-201 (1996). "Solubility and stability of taxol: effects of buffers and cyclodextrins."

* cited by examiner

*Primary Examiner* — Blessing M Fubara
(74) *Attorney, Agent, or Firm* — Nixon Peabody LLP

(57) ABSTRACT

A pharmaceutical solution of taxanes, its preparation method, a composition comprising said solution and its pharmaceutical combination package are disclosed. Said pharmaceutical solution comprises taxanes, a pH regulator and a solvent, wherein the pH regulator is a water-soluble acid.

12 Claims, No Drawings

PHARMACEUTICAL SOLUTION OF TAXANES COMPRISING PH REGULATOR AND PREPARATION METHOD THEREOF

CROSS REFERENCE TO RELATED APPLICATIONS

This application is a U.S.C. §371 National Application of International Application No. PCT/CN2010/077996 filed Oct. 22, 2014, which designates the U.S., and which claims benefit of Chinese Application No. 200910070931.8 filed Oct. 23, 2009, the content of which is incorporated herein by reference in its entirety.

FIELD OF INVENTION

The present invention relates to the field of pharmaceutical preparations technology. More specially, the present invention relates to a pharmaceutical solution of taxanes comprising a pH regulator and preparation method thereof.

BACKGROUND OF THE INVENTION

Taxanes include paclitaxel (trade name: Taxol) and docetaxel (trade name: Taxotem), two types of anti-cancer drugs of taxanes approved by Food & Drug Administration (FDA). They both belong to water-insoluble drugs, which can hardly be dissolved in water (about 4 μg/ml of water-solubility) and only 2%-4% is absorbed after oral administration. Hence, they can only be administrated intravenously. In order to enhance the water-solubility of paclitaxel, available paclitaxel injection is a colorless viscous concentrated solution prepared by a mixed solvent of polyoxyethylene castor oil and anhydrous ethanol in the ratio of 50:50 (v/v). Although the presence of composite solvent enhances the solubility of paclitaxel, a series of side effects are easily induced by the solubilizer, particularly polyoxyethylene castor oil, which is contained in this injection. The side effects of the available paclitaxel preparations after administration are severe: dyspnea, flushing face, palpitation and allergic reaction such as skin rash etc, which brings a lot of potential safety troubles and suffering to the patients. Similarly, there are problems in available docetaxel preparation. The clinical preparation of docetaxel is composed of Tween-80 solution and 13% ethanol solution. Although the addition of normal saline when administrating it to the patients through intravenous drip ameliorates solubility of docetaxel, yet Tween-80, utilized as a solubilizer in this injection, has an effect for hemolysis to some degree. Therefore, the available docetaxel preparation has less drug safety in the clinical application. Considering many drawbacks in available clinical applications, the research works on taxane drugs injection preparations become more and more active.

Fortner et al. (Am. J. Hosp. Pharm. (1975) 32, 582-584)) has reported a new dosage form for water-insoluble drug by dissolving them in a suitable solvent for injection to prepare a pharmaceutical solution, which was followed by adding with emulsion for injection when administrating it to the patients through intravenous drip. This dosage form has been taken more seriously ever since.

In the application entitled "Parenteral paclitaxel in a stable non-toxic formulation" filed by B. S Anderson (Chinese pat. No.: 97196934.5), the solvent of pharmaceutical solution was composed of PEG-400 and dimethylacetamide in the ratio of 3:1, in which the dimethylacetamide, utilized as a solubilizer by helping to enhance drug solubility though, increased effects of the preparation for inducing toxicity and side effect.

Therefore, dimethylacetamide utilized as a solubilizer may increase toxicity and side effect for the preparations. Zhou Lianfang et al. (Research progress on the toxicity of dimethylacetamide [J]. China Occupational Medicine, (2009), 36 (1): 66-67) pointed out that dimethylacetamide could cause multiple severe injuries on mice and rats, such as weight loss, atrophy of the retina, change of brain electric wave, as well as a lot of injuries to organs of lung, stomach, liver and kidney etc.

In the application entitled "Pharmaceutical composition containing hardly water soluble medicament" filed by Takeda Koichi et al. (Chinese Appl. No.:200680007345.3), the solvent of pharmaceutical solution was mainly composed of PEG-400 and oleic acid. As indicated by R. C. Roche (Handbook of Pharmaceutical Excipients, original $4^{th}$ edition: 476), the oleic acid might lead to hemocytocatheresis, namely effect of hemolysis. It is permitted only in non-injected preparations in Britain.

In the application entitled "A concentrated emulsion containing taxane compound and its using method" filed by Hu Yufang (Chinese Appl. No.:200410025522.3), the pharmaceutical solution was prepared into a mixed solvent containing surfactant, such as Tween-80, PVP and lecithin etc. These surfactants have both hemolytic activity and irritation.

Now, the key technology on which is focused mainly is the properties of selected material such as biocompatibility, in vivo tolerance and stability of dosage form. In despite of breakthrough that has been made in researches on some dosage forms, the clinical application is still restricted on account of low drug loading and short stabilization time, therefore making it impossible to reach an effectively therapeutic concentration. In the application developed by the present inventors and entitled "A taxane intravenous infusion preparation and its preparative method" (Chinese Appl. No.: 200810100234.8), no toxic solubilizer was contained, for example polyoxyethylene castor oil, Tween-80, dimethylacetamide, oleic acid and PVP etc, which finally makes its safety and stability improved significantly.

The present invention is a further research based on the Chinese patent application (Pat. Appl. No.: 200810100234.8). It was found that dispersion of emulsion in pharmaceutical solution, within a specific range of pH value, would make stabilization time and appearance better than that could be expected. The stabilization time was prolonged markedly; there was no floating oil on the surface of dispersed solution and the appearance was desirable. Clinically, safety and effectiveness of drugs were further improved. Consequently, the present invention belongs to an improved intravenous infusion preparation of taxanes and preparation method thereof.

SUMMARY OF THE INVENTION

The present invention provides a pharmaceutical composition of taxanes, prepared from two parts of pharmaceutical preparations: a pharmaceutical solution of taxanes and an emulsion. The pharmaceutical solution contains a pH regulator, which is used to adjust pH value to 2.0~4.0. The present invention is achieved by mixing the pharmaceutical solution and the emulsion in a ratio of 1:10~100 (WO, preferably 1:20~50 (v/v), most preferably 1:25(v/v).

According to present invention, due to the addition of pH regulator into the pharmaceutical solution of taxanes before used, which is used to adjust pH to 2.0~4.0, strong stability will be exhibited after mixing with an emulsion for injection.

According to the present invention, it provides a pharmaceutical solution of taxanes containing taxanes, a pH regulator and a solvent.

Preferably, the proportions of ingredients are as follows:

Taxanes 1~8% (g/ml)

pH regulator proper amount sufficient to adjust pH to 2.0~4.0

The balance is a solvent and additional pharmaceutical adjuvants, if necessary.

More preferably, the proportions of ingredients are as follows:

Taxanes 1—6% (g/ml)

pH regulator proper amount sufficient to adjust pH to 2.0~3.98

The balance is a solvent and additional pharmaceutical adjuvants, if necessary.

Wherein, the additional pharmaceutical adjuvants are the substances that are added during preparation of pharmaceutical solution according to the requirement, for example solubilizer, isotonic regulator, surfactant and chelating agent etc. In fact, whether adding these pharmaceutical adjuvants or not depends on properties of the taxanes, pH regulator and solvent.

Preferably, pH value is adjusted to 3.0~3.98 in the present invention.

According to the present invention, the taxanes are any one of taxanes, preferably commercially available paclitaxel or docetaxel.

According to present invention, the pH regulator is a water-soluble acid, including one or more kinds selected from the group consisting of citric acid, lactic acid, malic acid, hydrochloric acid, acetic acid, phosphoric acid and tartaric acid, preferably citric acid.

According to the present invention, the solvents include one or more solvents selected from the group consisting of PEG-200, PEG-300, PEG-400, PEG-600, propylene glycol, glycerol, anhydrous ethanol and water for injection, preferably PEG-400.

According to the present invention, a method of preparing solution of the present invention includes steps of dissolving taxanes and a pH regulator in a solvent. Additional pharmaceutical adjuvants may be added, if necessary.

Preferably, the method includes steps of: weighing paclitaxel or docetaxel; adding paclitaxel or docetaxel into a solvent; dissolved by heating and stirring at 50~100° C. or by shearing; diluting the mixture with the solvent; adjusting pH to 2.0~4.0 with the pH regulator; adding 0.01%~3% (g/ml) activated carbon for injection to perform adsorption by heating at 25~100° C. for 15~120 min; then filtering, separately packaging, cap-sealing and sterilizing to obtain the pharmaceutical solution of taxanes.

According to the present invention, it provides a kit comprising a pharmaceutical solution of taxanes and an emulsion loaded in two separate vessels that are arranged in a combined manner for clinical application. More particularly, the kit of the present invention comprises the pharmaceutical solution of taxanes and a medicinal emulsion in a ratio of 1:10~10:1, preferably 1:1, which are loaded in two separate plastic or glass bottles arranged in a combined manner in a same large vessel. Generally speaking, the present kit is designed desirably for a one-time use dosage.

According to the present invention, the emulsion is an oil-water mixed emulsified preparation, a non-uniformly dispersed system formed by dispersion of oils or oil-solutions in dispersion medium in the form of liquid drops. It includes oral emulsion and intravenous infusion emulsion. The emulsion of the present invention is intravenous infusion emulsion, preferably fat emulsion for intravenous infusion, for example 20% long/medium chain fat emulsion, 20% long chain fat emulsion etc.

According to the present invention, the emulsion of the present invention is commercially available emulsion for injection or the emulsion specifically prepared in accordance with the prior arts, comprising, generally speaking, oil for injection, emulsifier, antioxidant, isotonic regulator, pH regulator and water for injection.

According to the present invention, the oil for injection may be one or more oils selected from a group consisting of caprylic capric triglyceride, caprylic monoglyceride, caprylic diglyceride, caprylic triglyceride, *Ganoderma lucidum* spore oil, capric monoglyceride, capric diglyceride, capric triglyceride, caprylic capric monoglyceride, coix seed oil, Brucea Javanica oil, Herba Artemisiae Annuae oil, caprylic capric diglyceride, soybean oil, fish oil, linseed oil, helianthus annuus seed oil, evening primrose oil, sea buckthorn oil, zedoary turmeric oil, safflower seed oil, sesame oil, corn oil, elemene oil and garlic oil at a concentration of 1~30% (g/ml). The concentration (g/ml) of oils in emulsion is indicated by grams of oil per milliliter of the emulsion.

Preferably, the oil for injection is one or more oils selected from the group consisting of caprylic capric triglyceride and soybean oil at a concentration of 10~30% (g/ml).

According to the present invention, the emulsifier may be one or more emulsifiers selected from the group consisting of soybean phospholipid, yolk phospholipid, dimyristoyl phosphatidyl choline (DMPC), dipalmitoyl phosphatidylcholine (DPPC), distearoyl phosphatidylcholine (DSPC), dioleoylphosphatidylcholine(DOPC), palmitoyl-oleoyl phosphatidylcholine, distearoyl phosphatidylethanolamine (DSPE) and poloxamer 188 at a concentration of 0.5~5% (g/ml), preferably the emulsifier is one or more kinds selected from the group consisting of soybean phospholipid and yolk phospholipid at a concentration of 0.8~3% (g/ml). The concentration (g/ml) of the emulsifier in emulsion is indicated by grams of emulsifier per milliliter of the emulsion.

According to the present invention, the antioxidant is tocopherol at a concentration of 0~0.5% (g/ml), preferably 0~0.3% (g/ml).

According to the present invention, the isotonic regulator may be one or more kinds selected from the group consisting of glycerol, sorbitol, mannitol, glucose and sodium chloride etc, preferably glycerol.

According to the present invention, the pH regulator may be one or more kinds selected from the group consisting of citric acid, malic acid, hydrochloric acid, acetic acid, lactic acid, sodium carbonate, sodium bicarbonate and sodium hydroxide, preferably sodium hydroxide, with which pH value is adjusted to 6.0~9.0, preferably 6.5~8.5.

According to the present invention, the intravenous infusion emulsion is prepared in accordance with routine methods in the prior art: oil for injection is mixed with antioxidant and heated to 50~90° C., then an emulsifier is added and dissolved by stirring or shearing to obtain oil phase; isotonic regulator and stabilizer are added to a proper amount of water for injection and heated to 50~90° C., making them dissolved by stirring to obtain water phase; the resulted oil phase and water phase are mixed at 50~90° C. followed by emulsification by use of a shear emulsifying machine or stirring emulsification for 5-60 min at a rotation speed of 5000-30000 rpm to obtain a primary emulsion. The obtained primary emulsion is further emulsified, diluted to volume with water for injection and its pH value is adjusted to 6.0~9.0. Then the resultant emulsion is filtrated, separately packaged, charged with nitrogen, cap-sealed and sterilized, thus the emulsion is obtained.

Generally speaking, a method for preparing an emulsion includes steps of dissolving an emulsifier either in oil for injection or water. With respect to the present invention, the primary emulsion is further emulsified by high-pressure homogenizers under pressure of 5000-25000 psi. The sterilization method in the preparation of emulsions includes using rotary high-pressure steam sterilizer, circulating vapor or micro-porous filter membrane, wherein the high-temperature sterilization temperature is 100~121° C. and the time is 8~45 min. The filtrating equipment includes but is not limited to micro-porous filter membrane, sand-filter rod, sintered filter funnel or capsule filter etc. The final emulsion is a white or off-white emulsified liquid with opalescence, and the average particle size of the emulsion micro-particles ranges from 100 to 500 nm, with a pH value from 6.0~9.0.

According to the present invention, it provides a method of using the pharmaceutical solution of taxanes, including dispersing the pharmaceutical solution of taxanes into a medicinal emulsion in a ratio of 1:10~100 by volume, preferably 1:25 by volume, and shaking well for intravenous drip. Alternatively, the pharmaceutical solution dispersed by emulsion can be added into normal saline or glucose solution for injection, when used.

Advantages of the present invention are shown by the following experiment data.

1. Evaluation of Stability of Dispersion Liquid of Paclitaxel Intravenous Injections before Administration The paclitaxel intravenous injection prepared in accordance with the method of Example 1 was taken as an example to make research on a variety of changes in drug content, particle size and appearance.

Investigation method: 4 ml pharmaceutical solution was dispersed into 100 ml emulsion and shaken well. The drug content and particle size of the dispersion solution were determined at different time-points by HPLC and a particle size analyzer, respectively; when determining the drug content at the different time-points, appropriate amount of dispersion solutions was extracted with injectors and filtrated firstly by 0.45 μm micro-porous filter membrane and then the drug contents in filtrates were determined to calculate labeled percentage amount, which was used to estimate whether drug crystal was precipitated or not; the particle size was measured directly; and the appearance was observed with naked eyes. The results are summarized in Table 1.

TABLE 1

Investigation on stability of dispersion solution of paclitaxel intravenous injections before administration exemplified by Example 1 (the emulsion for dispersion was self-prepared emulsion)

| | Time(day) | | | | | |
|---|---|---|---|---|---|---|
| | 0 | 1 | 2 | 3 | 4 | 5 |
| Content(%) | 100.0 | 99.7 | 99.6 | 101.0 | 100.5 | 96.4 |
| Particle size(nm) | 130.1 | 135.0 | 127.8 | 129.0 | 134.7 | 138.1 |
| Appearance | having a better appearance without floating oil within 5 days | | | | | |

Discussion:

As shown in the results of Table 1, there were hardly any changes in drug content of the dispersion solution of paclitaxel intravenous injection, prepared in accordance with the method of Example 1, within 5 days before administration. This suggested that no paclitaxel crystal precipitation occurred within this time period. Similarly, the particle size did not show any significant change within stability time. As a result of this, the present paclitaxel intravenous injection totally complied with requirement for clinical application.

2. Evaluation of Stability of Dispersion Liquid of Docetaxel Intravenous Injections before Administration The docetaxel intravenous injection prepared in accordance with the method of Example 2 was taken as an example to make research on a variety of changes in drug content, particle size and appearance.

Investigation method: 4 ml pharmaceutical solution was dispersed into 100 ml emulsion and shaken well. The drug content and particle size of the dispersion solution were determined at different time-points by HPLC and a particle size analyzer, respectively; when determining the drug content at the different time-points, appropriate amount of dispersion solutions was extracted with injectors and filtrated firstly by 0.45 μm micro-porous filter membrane and then the drug contents in filtrates were determined to calculate labeled percentage amount, which was used to estimate whether drug crystal was precipitated or not; the particle size was measured directly; and the appearance was observed with naked eyes. The results are summarized in Table 2.

TABLE 2

Investigation on stability of dispersion solution of docetaxel intravenous injection before administration exemplified by Example 2 (the emulsion for dispersion was self-prepared emulsion)

| | Time (day) | | | | | |
|---|---|---|---|---|---|---|
| | 0 | 2 | 4 | 6 | 8 | 10 |
| Content (%) | 100.0 | 100.5 | 99.7 | 99.2 | 100.7 | 100.1 |
| Particle size(nm) | 210 | 135.0 | 127.8 | 129.0 | 134.7 | 138.1 |
| Appearance | having a better appearance without floating oil within 10 days | | | | | |

Discussion:

As shown in the results of Table 2, there were hardly any changes in drug content of the dispersion solution of docetaxel intravenous injection, prepared in accordance with the method of Example 2, within at least 10 days before administration. Half a month later, this sample was assayed again, and the drug content remained unchanged. When assayed on the $20^{th}$ day from the beginning, the labeled percentage amount was decreased to 90.2%. This suggested that no docetaxel crystal precipitation occurred within at least 15 days. Similarly, the particle size did not show any significant change within stabilization time period. As a result of this, the present docetaxel intravenous injection totally complied with requirement for clinical application.

3. Stability Evaluation of Dispersion Liquid of Emulsion within the Range of Specific pH Value In order to show substantial characteristic and unanticipated result of the present invention, comparison had been carried out in stability of dispersion solution between pH-specified and pH-routine pharmaceutical solutions. In the present invention, the specified pH value range was 2.0~4.0, while routine pH value was 4.0 or higher.

a) Preparation of Test Sample

According to the method of Example 16, 4 pharmaceutical solutions were prepared. The pH value was respectively regulated to 2.04, 2.68, 3.20, and 3.98 with citric acid, and similarly the pharmaceutical solutions were dispersed in commercially available emulsions in light of method of Example 16 in a ratio of 1:25 by volume, shaken well to obtain the test sample.

b) Preparation of Control Sample

According to the method of Example 16, 4 pharmaceutical solutions were prepared. The pH value was regulated with sodium hydroxide or hydrochloric acid to 4.50, 5.61, 6.87 and 7.53, and similarly the pharmaceutical solutions were dispersed in commercially available emulsions in light of method of Example 16 in a ratio of 1:25 by volume, shaken well, then the drug content was determined to obtain the control samples.

c) Comparison Result of Stability of Dispersion Solutions

The drug content and particle size of the test sample and control sample were determined at different time-points by HPLC and a particle size analyzer, respectively. When determining the drug content at the different time-points, appropriate amount of dispersion solutions was extracted with injectors and filtrated firstly by 0.45 μm micro-porous filter membrane and then the drug contents in filtrates were determined to calculate labeled percentage amount, which was used to estimate whether drug crystal was precipitated or not. In addition, the particle size was measured directly and the appearance was observed with naked eyes. The results are summarized in Table 3.

TABLE 3 investigation on stability of dispersion solution between control and test sample (the emulsion for dispersion was commercially available)

A. Comparison of percentage

| pH series | 8 h | 10 h | 12 h | 14 h | 16 h | 18 h |
|---|---|---|---|---|---|---|
| 2.04 | 99.8% | 98.9% | 100.0% | 99.5% | 96.6% | 94.0% |
| 2.68 | 100.2% | 100.4% | 98.6% | 99.1% | 98.7% | 98.0% |
| 3.20 | 99.8% | 100.1% | 99.0% | 102.0% | 101.7% | 99.4% |
| 3.98 | 101.3% | 99.5% | 98.9% | 100.8% | 97.0% | 95.1% |
| 4.50 | 99.4% | 97.0% | 90.5% | | | |
| 5.61 | 101.2% | 94.1% | 85.9% | | | |
| 6.87 | 99.5% | 90.3% | 80.4% | | | |
| 7.53 | 98.6% | 90.4% | 80.2% | | | |

B. Comparison of particle size

| pH series | 8 h | 10 h | 12 h | 14 h | 16 h | 18 h |
|---|---|---|---|---|---|---|
| 2.04 | 217 nm | 220 nm | 230 nm | 210 nm | 229 nm | 240 nm |
| 2.68 | 210 nm | 221 nm | 211 nm | 224 nm | 218 nm | 234 nm |
| 3.20 | 215 nm | 222 nm | 224 nm | 212 nm | 225 nm | 234 nm |
| 3.98 | 210 nm | 208 nm | 210 nm | 228 nm | 230 nm | 228 nm |
| 4.50 | 217 nm | 231 nm | 243 nm | | | |
| 5.61 | 222 nm | 250 nm | 248 nm | | | |
| 6.87 | 214 nm | 246 nm | 257 nm | | | |
| 7.53 | 216 nm | 250 nm | 261 nm | | | |

C. Comparison of appearance

| Sample | 8 h | 10 h | 12 h | 14 h | 16 h | 18 h |
|---|---|---|---|---|---|---|
| 2.04 | NO | NO | NO | NO | NO | YES |
| 2.68 | NO | NO | NO | NO | NO | NO |
| 3.20 | NO | NO | NO | NO | NO | NO |
| 3.98 | NO | NO | NO | NO | NO | YES |
| 4.50 | YES | MORE | SEVERE | | | |
| 5.61 | YES | MORE | SEVERE | | | |
| 6.87 | YES | MORE | SEVERE | | | |
| 7.53 | YES | MORE | SEVERE | | | |

YES = floating oil; NO = no floating oil;
MORE = more floating oil; SEVERE = severe floating oil Discussion:

Stabilization time of emulsion dispersion solution of the pharmaceutical solution of the present invention having specific pH value within the range of 2~4 was far longer than the control dispersion solution with pH value of 4 or more. As for the appearance, no floating oil had occurred in the dispersion solution of the present invention with a pH value within the range of 2~4, which having a better appearance and overcoming the drawback of floating oil unexpectedly, while more floating oil in the dispersion solution of control sample with a pH value of 4 or more, having a great deal of oil grease adhering on wall and the floating oil increased with time elapsed. Moreover, the particle size did not show any significant change before drug precipitated, and tended to become larger with drug precipitated.

All these findings suggested that the emulsion dispersion of the pharmaceutical solution with the specified pH value within the range of 2~4 showed considerably improved stability compared with the control dispersion solution with a pH value of 4 or higher. What is more important, stabilization time of dispersion solution had been prolonged, and the drawback of floating oil had been overcome. Hence, the preparation quality of the present invention had been improved markedly, enhancing safety and efficacy for clinical application.

4. Stability Contrast Test between the Present Invention and Comparative Patent Containing Dimethyl Acetylamide As suggested in Chinese pat. (Patent No.: 97196934.5), dimethyl acetylamide was added into PEG-400 in a ratio of 1:3 with a drug loading of 25 mg/ml. A pharmaceutical solution was prepared in accordance with the method of this patent as a contrast solution, and test solution was prepared in accordance with the Example 16. 4 ml test and contrast solutions were dispersed respectively into 100 ml commercially available emulsions in Example 16, shaken well to obtain measuring sample. The drug content of the dispersion solution was determined at different time-points by HPLC. When determining the drug content at the different time-points, appropriate amounts of dispersion solution was extracted with injectors and filtrated firstly by 0.45 μm micro-porous filter membrane and then the drug contents in filtrates were determined to calculate labeled percentage amount, which was used to estimate whether drug crystal was precipitated or not. In addition, the appearance was observed with naked eyes. The results are summarized in Table 4.

TABLE 4

Investigation on stability of dispersion solution of the preparation of the present invention and dimethyl acetylamide-containing preparation of contrast patent (the emulsion for dispersion was commercially available emulsion)

| | Time | | | | |
|---|---|---|---|---|---|
| | 6 h | 8 h | 10 h | 15 h | 17 h |
| Present preparation | 100.8% | 101.1% | 100.4% | 99.5% | 97.3% |
| Contrast preparation | 94.7% | 90.2% | 86% | | |
| Appearance | No floating oil occurred in present invention preparation within 17 hours, while there was more oil in contrast preparation. | | | | |

Discussion:

As shown in the results, both of dispersion solutions, though dispersed in the same commercially available emulsion as a solvent, exhibited different stabilization times: the preparation of the present invention had a stabilization time of 17 hours or more, while the contrast preparation containing dimethyl acetylamide has a stabilization time less than 6 hours. It was thus clear that the present invention had great significant advantages and unanticipated effects in comparison with Chinese pat. (97196934.5). As for the appearance, no floating oil had been observed in the dispersion solution of the present invention, while there was more floating oil in contrast preparation containing dimethyl acetylamide even with a great deal of oil grease adhering on wall.

5. Stability Contrast Test between the Present Invention and Comparative Patent Containing Oleic Acid As suggested in Chinese patent application (Patent Appl. No.: 200680007345.3), oleic acid was added based on PEG-400 in an amount of 0.01~5%. In light of this method, 0.3%, 1.0% and 5.0% oleic-acid/PEG-400 solutions were prepared respectively, which was used as a solvent to prepare 25 mg/ml paclitaxel solution as a contrast solution. A pharmaceutical solution was prepared in accordance with the Example 16 as a test solution. 4 ml test and contrast solutions were dispersed respectively into 100 ml commercially available emulsions in Example 16, shaken well to obtain a measuring sample. The drug contents of the dispersion solution were determined at different time-points by HPLC. When determining the drug content at the different time-points, appropriate amount of dispersion solutions was extracted with injectors and filtrated firstly by 0.45 μm micro-porous filter membrane and then the paclitaxel contents in filtrates were determined to calculate labeled percentage amount, which was used to estimate whether drug crystal was precipitated or not. In addition, the appearance was observed with naked eyes. The results are summarized in Table 5.

TABLE 5

Investigation on stability of dispersion solution of the preparation of the present invention and oleic acid-containing preparation of contrast patent (the emulsion for dispersion was commercially available emulsion)

| Sample | 6 h | 8 h | 10 h | 15 h | 17 h |
|---|---|---|---|---|---|
| Present preparation | 100.8% | 101.1% | 100.4% | 99.5% | 97.3% |
| 0.3% oleic acid | 93.1% | 88.5% | 81.1% | | |
| 1.0% oleic acid | 89.4% | 82.6% | 76.7% | | |
| 5.0% oleic acid | 81.6% | 76.0% | 72.5% | | |
| Appearance | No floating oil occurred in present invention preparation within 17 hours, while there was more oil in contrast preparation. | | | | |

Discussion:

As shown in the results, both of dispersion solutions, though dispersed in the same commercially available emulsion as a solvent, exhibited different stabilization times: the oleic acid-containing contrast preparation was less than 6 hours and its stability decreased with the amount of oleic acid increased after being diluted. This suggested that the oleic acid had a destructive effect on stability of preparation. In contrast, the preparation of the present invention was as long as 17 hours or more. It was thus clear that the present invention had great significant advantages and unanticipated effects in comparison with Chinese patent application (Patent Appl. No.: 200680007345.3). As for the appearance, no floating oil had been observed in the dispersion solution of the present invention, while there was more floating oil in contrast preparation even with a great deal of oil grease adhering on wall.

6. Stability Contrast Test between the Present Invention and Comparative Patent Containing Surfactant As suggested in Chinese patent application (Patent Appl. No.: 200410025522.3), it was mainly composed of paclitaxel, Tween-80, PVP, lecithin and solvent for injection. The closest method to the present invention was Example 3, having a formulation of 1.8 g paclitaxel, 22 g phospholipid, 40 g propylene glycol, balanced with anhydrous ethanol to 100 ml. In light of this method, a pharmaceutical solution was prepared as a contrast solution, and paclitaxel solution was prepared according to method of Example 16 of the present invention as a test solution. 4 ml test and contrast solutions were dispersed respectively into 100 ml commercially available emulsions in Example 16, shaken well to obtain measuring sample. The drug content of the dispersion solution was determined at different time-points by HPLC. When determining the drug content at the different time-points, appropriate amount of dispersion solution was extracted with injectors and filtrated firstly by 0.45 μm micro-porous filter membrane and then the paclitaxel contents in filtrates were determined to calculate labeled percentage amount, which was used to estimate whether drug crystal was precipitated or not. In addition, the appearance was observed with naked eyes. The results are summarized in Table 6.

TABLE 6

Investigation on stability of dispersion solution of the preparation of the present invention and surfactant-containing preparation of contrast patent (the emulsion for dispersion was commercially available emulsion)

| Sample | 6 h | 8 h | 10 h | 15 h | 17 h |
|---|---|---|---|---|---|
| Present preparation | 100.8% | 101.1% | 100.4% | 99.5% | 97.3% |
| Contrast preparation | 99.6% | 94.4% | | | |
| Appearance | No floating oil found in the present invention preparation within 17 hours, while there was more oil in contrast preparation. | | | | |

Discussion:

As shown in the results, both of dispersion solutions, though dispersed in the same commercially available emulsion as a solvent, exhibited different stabilization times: the contrast preparation containing surfactant had a stabilization time less than 8 hours, while the preparation of the present invention had a stabilization time of 17 hours or more. As for the appearance, no floating oil had occurred in the dispersion solution of the present invention, but there was more floating oil in contrast preparation containing surfactant with a great deal of oil grease adhering on wall. It was thus clear that the present invention had great significant advantages and unanticipated effects in comparison with Chinese patent application (Patent Appl. No.: 200410025522.3).

The intravenous infusion preparation of taxanes of the present invention offers some advantages as follows:

(1) The preparations of the present invention have excellent safety. The preparations of the present invention do not contain any solubilizer having the toxicity and side effects, such as polyoxyethylene castor oil, tween-80, dimethylacetamide, oleic acid and polyvidone etc., wherein, polyoxyethylene castor oil and tween-80 have poor safety for causing serious hemolysis and allergic reaction. Oral $LD_{50}$ of dimethylacetamide for mice is 4.620 g/kg. By comparison, non-toxic and non-irritative PEG-400 is preferably utilized as solvent for injection in the present invention, and its oral $LD_{50}$ for mice reaches 28.9 g/kg, which is 6.3 times than that of dimethylacetamide. So, PEG-400 is proven to be a safe solvent for injection. In addition, as indicated by R. C. Roche (Handbook of pharmaceutical excipients, original 4th edition: p 476), oleic acid might cause hemocytocatheresis, i.e., having hemolytic activity, which is allowed to use for non-injected preparations only. Consequently, absence of solubilizer having toxicity and side effects is a real highlight of the present invention.

(2) The preparations of the present invention have excellent stability. Stability of dispersion solution prepared by using the solution of the present invention was improved markedly. This makes stabilization time of dispersion solution extended significantly, solves the problem of floating oil more than expected, and further improves stability of dispersion solution.

BEST MODES OF THE INVENTION

In order to demonstrate the substantial advantage and unexpected effect of the present invention, the present invention is carried out according to following examples, but not limited to these examples.

EXAMPLE 1

Paclitaxel Intravenous Infusion Preparation and a Kit Thereof a) Preparation of the pharmaceutical solution: 2.5 g paclitaxel was added to a proper amount of PEG-400, heated to 70° C. to dissolve by shearing, and diluted with PEG-400 to 100 ml. Citric acid was added to adjust pH value to 3.24 and 0.2 g activated carbon for injection was added to perform adsorption at 25° C. for 30 min. Next, the solution was filtrated by micro-porous filter membrane, separately packaged, cap-sealed, sterilized by a rotary high-pressure steam sterilizer at 121° C. for 30 min, and the paclitaxel solution was thus obtained;

b) Preparation of the emulsion: 100 g soybean oil and 100 g caprylic capric triglyceride were heated to 70° C. in water bath, into which 20 g soybean phospholipid for injection was added and dissolved by shearing, and stirred well to obtain the oil phase; 22.5 g glycerol and 10 g poloxamer 188 were added into 750 ml water for injection, and stirred at 70° C. to dissolve the glycerol and poloxamer 188 to obtain the water phase; the oil phase was mixed with the water phase at 70° C., and followed by emulsification using a shear emulsifying machine for 15 min at a rotation speed of 15000 rpm to obtain a primary emulsion. The primary emulsion was further emulsified by a high-pressure homogenizer under a pressure of 15000 psi. The emulsion was diluted to 1000 ml with water for injection, and its pH value was adjusted to 7.50 with sodium hydroxide solution. The emulsion was filtrated by micro-porous filter membrane, then the filtrate was separately packaged, charged with nitrogen, cap-sealed and sterilized by a rotary high-pressure steam sterilizer at 121° C. for 15 min to obtain the emulsion. The average particle size of the emulsion micro-particles was measured to be 130 nm with the pH value of 6.99.

Afore-obtained paclitaxel solution and medicinal emulsion were respectively loaded in plastic or glass bottles, which were packaged up in a ratio of 1:1 in a same large vessel.

When used, the paclitaxel solution can be added and evenly dispersed in the medicinal emulsion in a ratio of 1:25 by volume to perform intravenous drip directly; or the pharmaceutical solution can also be firstly added into the emulsion and then a normal saline injection with a predetermined amount of normal saline or glucose solution for injection is added to perform the injection.

EXAMPLE 2

Docetaxel Intravenous Infusion Preparation and a Kit Thereof a) Preparation of the pharmaceutical solution: 2.5 g docetaxel was added to a proper amount of PEG-400, heated to 80° C. to dissolve by shearing, and diluted with PEG-400 to 100 ml. Citric acid was added to adjust pH value to 3.50 and 0.2 g activated carbon for injection was added to perform adsorption at 25° C. for 30 min. Next, the solution was filtrated by a capsule filter, sterilized by 0.22 μm micro-porous filter membrane, separately packaged and cap-sealed and the docetaxel solution was thus obtained;

b) Preparation of the emulsion: 200 g soybean oil for injection was heated to 80° C. in water bath, into which 12 g yolk phospholipid for injection was added and dissolved by stirring to obtain the oil phase. 22.5 g glycerol was added to 680 ml water for injection and dissolved by stirring and heated to 80° C. to obtain the water phase. The oil phase was mixed with the water phase at 80° C., and followed by emulsification using a shear emulsifying machine for 15 min at a rotation speed of 18000 rpm to obtain a primary emulsion. The primary emulsion was further emulsified by a high-pressure homogenizer under a pressure of 20000 psi. The emulsion was diluted to 1000 ml with water for injection, and its pH value was adjusted to 7.10 by sodium hydroxide solution. The emulsion was filtrated by micro-porous filter membrane, then the filtrate was separately packaged, charged with nitrogen, cap-sealed and sterilized by a rotary high-pressure steam sterilizer at 121° C. for 15 min to obtain the emulsion. The average particle size of the emulsion micro-particles was measured to be 210 nm with the pH value of 6.57.

Afore-obtained docetaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:25 by volume to perform intravenous drip directly.

EXAMPLE 3

Paclitaxel Intravenous Infusion Preparation and a Kit Thereof a) Preparation of the pharmaceutical solution: 3 g paclitaxel was added to a proper amount of PEG-400, heated to 90° C. to dissolve by stirring, and diluted with PEG-400 to 100 ml. Citric acid was used to adjust pH value to 3.14. 0.5 g activated carbon for injection was added to perform adsorption at 25° C. for 45 min. Next, the solution was filtrated by micro-porous filter membrane, separately packaged, cap-sealed and sterilized by a rotary high-pressure steam sterilizer at 115° C. for 30 min, and the paclitaxel solution was thus obtained;

b) Preparation of the emulsion: a mixture of 50 g soybean oil and 50 g caprylic capric triglyceride was heated to 55° C. in water bath, into which 12 g yolk phospholipid for injection was added to dissolve by shearing to obtain the oil phase; 25 g glycerol was added into 800 ml water for injection, and stirred at 55° C. to dissolve the glycerol to obtain the water phase; the oil phase was mixed with the water phase at 55° C., and followed by emulsification using a shear emulsifying machine for 20 min at a rotation speed of 22000 rpm to obtain a primary emulsion. The primary emulsion was further emulsified by a high-pressure homogenizer under a pressure of 18000 psi. The emulsion was diluted to 1000 ml with water for injection, and its pH value was adjusted to 7.80 by sodium hydroxide solution. The emulsion was filtrated by a capsule filter, then the filtrate was separately packaged, charged with nitrogen, cap-sealed and sterilized by a rotary high-pressure steam sterilizer at 115° C. for 30 min to obtain the emulsion. The average particle size of the emulsion micro-particles was measured to be 178.1 nm with the pH value of 7.18.

Afore-obtained paclitaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:50 by volume to perform intravenous drip directly.

EXAMPLE 4

Docetaxel Intravenous Infusion Preparation and a Kit Thereof a) Preparation of the pharmaceutical solution: 4.0 g docetaxel was added to a proper amount of PEG-400, heated to 55° C. to dissolve by shearing, and diluted with PEG-400 to 100 ml. Citric acid was added to adjust pH value to 3.04. 1.0 g activated carbon for injection was added to perform adsorption at 60° C. for 15 min. Next, the solution was filtrated by micro-porous filter membrane, separately packaged, cap-sealed and sterilized by a rotary high-pressure steam sterilizer at 115° C. for 30 min and the docetaxel solution was thus obtained;
b) Preparation of the emulsion: 150 g soybean oil, 150 g caprylic capric triglyceride and 2 g tocopherol were mixed, heated to 85° C. in water bath, into which 10 g yolk phospholipid for injection and 10 g soybean phospholipid were added to dissolve by shearing to obtain the oil phase; 22 g glycerol and 10 g poloxamer-188 were added into 650 ml water for injection, and heated to 85° C. to obtain the water phase; the oil phase was mixed with the water phase at 85° C., and followed by emulsification using a shear emulsifying machine for 30 min at a rotation speed of 5000 rpm to obtain a primary emulsion. The primary emulsion was further emulsified by a high-pressure homogenizer under a pressure of 25000 psi. The emulsion was diluted to 1000 ml with water for injection, and its pH value was adjusted to 7.51 by sodium hydroxide solution. The emulsion was filtrated by sand-filter rod, then the filtrate was separately packaged, charged with nitrogen, cap-sealed and sterilized by a rotary high-pressure steam sterilizer at 115° C. for 30 min to obtain the emulsion. The average particle size of the emulsion micro-particles was measured to be 280.2 nm with the pH value of 7.05.

Afore-obtained docetaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:30 by volume to perform intravenous drip directly.

EXAMPLE 5

Paclitaxel Intravenous Infusion Preparation and a Kit Thereof a) Preparation of the pharmaceutical solution: 4.0 g paclitaxel was added to a proper amount of PEG-400, to dissolve at 82° C. by shearing, and diluted with PEG-400 to 100 ml. Citric acid was used to adjust pH value to 3.98. 0.05 g activated carbon for injection was added to perform adsorption at 80° C. for 20 min. Next, the solution was filtrated by sand-filter rod, separately packaged, cap-sealed and sterilized by circulating vapor at 100° C. for 45 min, and the paclitaxel solution was thus obtained;
b) Preparation of the emulsion: 200 g caprylic capric triglyceride was heated to 65° C. in water bath to obtain the oil phase; 9 g soybean phospholipid, 9 g yolk phospholipid and 22.5 g glycerol were added into 700 ml water for injection, stirred well and heated to 65° C. to obtain the water phase; the oil phase was mixed with the water phase at 65° C., and followed by emulsification using a shear emulsifying machine for 28 min at a rotation speed of 6000 rpm to obtain a primary emulsion. The primary emulsion was further emulsified by a high-pressure homogenizer under a pressure of 10000 psi. The emulsion was diluted to 1000 ml with water for injection, and its pH value was adjusted to 6.58 by sodium hydroxide solution. The emulsion was filtrated by a sintered filter funnel, separately packaged, charged with nitrogen, cap-sealed and sterilized by a rotary high-pressure steam sterilizer at 121° C. for 8 min to obtain the emulsion. The average particle size of the emulsion micro-particles was measured to be 150 nm with the pH value of 6.01.

Afore-obtained paclitaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:70 by volume to perform intravenous drip directly.

EXAMPLE 6

Docetaxel Intravenous Infusion Preparation and a Kit Thereof a) Preparation of the pharmaceutical solution: 5.0 g docetaxel was added to a mixture of 50 g PEG-400 and 35 g anhydrous ethanol, heated to 55° C. to dissolve by shearing, and diluted with anhydrous ethanol to 100 ml. Hydrochloric acid was used to adjust pH value to 2.02. 1.0 g activated carbon for injection was added to perform adsorption at 90° C. for 110 min. Next, the solution was filtrated by a capsule filter, separately packaged, cap-sealed and sterilized by circulating vapor at 100° C. for 45 min, and the docetaxel solution was thus obtained;
b) Preparation of the emulsion: a mixture of 70 g linseed oil, 80 g helianthus annuus seed oil, 50 g caprylic monoglyceride, 50 g caprylic triglyceride and 4 g tocopherol were heated to 75° C. in water bath, into which 5 g DMPC and 3 g DPPC were added to dissolve by stirring to obtain the oil phase; 21.0 g glycerol was added into 620 ml water for injection, heated to 75° C. and dissolved by stirring to obtain the water phase; the oil phase was mixed with the water phase at 75° C., and followed by emulsification using a shear emulsifying machine for 8 min at a rotation speed of 30000 rpm to obtain a primary emulsion. The primary emulsion was further emulsified by a high-pressure homogenizer under a pressure of 12000 psi. The emulsion was diluted to 1000 ml with water for injection, and its pH value was adjusted to 9.00 by sodium hydroxide solution. The emulsion was filtrated by a sintered filter funnel, separately packaged, charged with nitrogen, cap-sealed and sterilized by a rotary high-pressure steam sterilizer at 121° C. for 10 min to obtain the emulsion. The average particle size of the emulsion micro-particles was measured to be 259 nm with the pH value of 8.48.

Afore-obtained docetaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:80 by volume to perform intravenous drip directly.

EXAMPLE 7

Paclitaxel Intravenous Infusion Preparation and a Kit Thereof a) Preparation of the pharmaceutical solution: 1.0 g Paclitaxel was added to a mixture of 30 g propylene glycol, 60 g PEG-200 and 5 g water for injection to dissolve by shearing at 70° C., and diluted with water for injection to 100 ml. Hydrochloric acid was added to adjust pH value to 2.54 and 2.6 g activated carbon for injection to perform adsorption at 25° C. for 90 min. Next, the solution was filtrated by a sintered filter funnel, separately packaged, cap-sealed and sterilized by circulating vapor at 100° C. for 45 min, and the paclitaxel solution was thus obtained;
b) Preparation of the emulsion: 6 g coix seed oil, 6 g brucea javanica oil, 10 g capric monoglyceride, 3 g corn oil, 5 g caprylic diglyceride and 0.5 g tocopherol were mixed, heated to 70° C. in water bath and stirred well to obtain the oil phase; 1 g poloxamer for injection, 4 g yolk phospholipid, 1 g DSPE and 25 g glycerol were added into 850 ml water for injection, dispersed by shearing and heated to 70° C. to obtain the water phase; the oil phase was mixed with the water phase at 70° C., and followed by emulsification by stirring for 10 min to obtain a primary emulsion. The primary emulsion was further emulsified by a high-pressure homogenizer under a pressure of 7000 psi. The emulsion was diluted to 1000 ml with water for injection, and its pH value was adjusted to 8.75 by sodium hydroxide solution. The emulsion was filtrated by micro-porous filter membrane, separately packaged, charged with nitrogen, cap-sealed and sterilized by a rotary high-pressure steam sterilizer at 115° C. for 30 min to obtain the emulsion. The average particle size of the emulsion micro-particles was measured to be 110 nm with the pH value of 8.31.

Afore-obtained paclitaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:10 by volume to perform intravenous drip directly.

EXAMPLE 8

Docetaxel Intravenous Infusion Preparation and a Kit Thereof a) Preparation of the pharmaceutical solution: 3.0 g docetaxel was added to a mixture of 60 g PEG-600, 10 g glycerol and 20 g anhydrous ethanol, dissolved by stirring at 85° C., and diluted with anhydrous ethanol to 100 ml. Hydrochloric acid was added to adjust pH value to 2.68 and 1.4 g activated carbon for injection to perform adsorption at 50° C. for 60 min. Next, the solution was filtrated by a capsule filter, separately packaged, cap-sealed and sterilized by a rotary high-pressure steam sterilizer at 121° C. for 15 min, and the docetaxel solution was thus obtained;
b) Preparation of the emulsion: 200 g fish oil and 2 g tocopherol were mixed, heated to 80° C. in water bath and stirred well to obtain the oil phase; 12 g yolk phospholipid, and 22.5 g glycerol were added into 800 ml water for injection, dispersed by shearing and heated to 80° C. to obtain the water phase; the oil phase was mixed with the water phase at 80° C., and followed by emulsification using a shear emulsifying machine for 25 min at a rotation speed of 7000 rpm to obtain a primary emulsion. The primary emulsion was further emulsified by a high-pressure homogenizer under a pressure of 25000 psi. The emulsion was diluted to 1000 ml with water for injection, and its pH value was adjusted to 8.10 by sodium hydroxide solution. The emulsion was filtrated by a capsule filter, separately packaged, charged with nitrogen, cap-sealed and sterilized by a rotary high-pressure steam sterilizer at 121° C. for 15 min to obtain the emulsion. The average particle size of the emulsion micro-particles was measured to be 208.5nm with the pH value of 7.60.

Afore-obtained docetaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:25 by volume to perform intravenous drip directly.

EXAMPLE 9

Paclitaxel Intravenous Infusion Preparation and a Kit Thereof a) Preparation of the pharmaceutical solution: 4.0 g paclitaxel was added to 80 g PEG-400, dissolved by shearing at 78° C., and diluted with PEG-400 to 100 ml. Acetic acid was added to adjust pH value to 3.30 and 0.3 g activated carbon for injection was added to perform adsorption at 30° C. for 70 min. Next, the solution was filtrated by a capsule filter, separately packaged, cap-sealed and sterilized by a rotary high-pressure steam sterilizer at 121° C. for 12 min, and the paclitaxel solution was thus obtained;
b) Preparation of the emulsion: 60 g herba artemisiae annuae oil, 30 g caprylic capric diglyceride, 65 g capric triglyceride, 65 g caprylic capric monoglyceride, 32 g safflower seed oil, 30 g sesame oil, 18 g sea buckthorn oil and 4.5 g tocopherol were mixed, heated to 78° C. in water bath and stirred well to obtain the oil phase; 22.5 g glycerol, 40 g yolk phospholipid and 10 g poloxamer 188 were added into 600 ml water for injection, dissolved by shearing and heated to 70° C. to obtain the water phase; the oil phase was mixed with the water phase at 78° C., and followed by emulsification using a shear emulsifying machine for 20 min at a rotation speed of 8500 rpm to obtain a primary emulsion. The primary emulsion was further emulsified by a high-pressure homogenizer under a pressure of 25000 psi. The emulsion was diluted to 1000 ml with water for injection, and its pH value was adjusted to 6.86 by sodium hydroxide solution. The emulsion was filtrated by micro-porous filter membrane, separately packaged, charged with nitrogen, cap-sealed and sterilized by a rotary high-pressure steam sterilizer at 121° C. for 10 min to obtain the emulsion. The average particle size of the emulsion micro-particles was measured to be 287.2nm with the pH value of 6.55.

Afore-obtained paclitaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:60 by volume to perform intravenous drip directly.

EXAMPLE 10

Docetaxel Intravenous Infusion Preparation and a Kit a) Preparation of the pharmaceutical solution: 2.5 g docetaxel was added to 90 g PEG-400, heated to 80° C. to dissolve by stirring, and diluted with PEG-400 to 100 ml. Acetic acid was added to adjust pH value to 3.30 and 0.5 g activated carbon for injection was added to perform adsorption at 25° C. for 45 min. Next, the solution was filtrated by a capsule filter, separately packaged, cap-sealed and sterilized by a rotary high-pressure steam sterilizer at 115° C. for 30 min, and the docetaxel solution was thus obtained;

b) Preparation of the emulsion: 150 g soybean oil for injection and 50 g ganoderma lucidum spore oil were mixed, heated to 70° C. in water bath, into which 12 g yolk phospholipid for injection was added and dissolved shearing to obtain the oil phase; 22.5 g glycerol was added into 680 ml water for injection, dissolved by stirring and heated to 70° C. to obtain the water phase; the oil phase was mixed with the water phase at 70° C., and followed by emulsification using a shear emulsifying machine for 5 min at a rotation speed of 27000 rpm to obtain a primary emulsion. The primary emulsion was further emulsified by a high-pressure homogenizer under a pressure of 15000 psi. The emulsion was diluted to 1000 ml with water for injection, and its pH value was adjusted to 8.52 by sodium hydroxide solution. The emulsion was filtrated by micro-porous filter membrane, separately packaged, charged with nitrogen, cap-sealed and sterilized by a rotary high-pressure steam sterilizer at 117° C. for 20 min to obtain the emulsion. The average particle size of the emulsion micro-particles was measured to be 220nm with the pH value of 8.02.

Afore-obtained docetaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:100 by volume to perform intravenous drip directly.

EXAMPLE 11

Paclitaxel Intravenous Infusion Preparation and a Kit Thereof a) Preparation of the pharmaceutical solution: 2.5 g paclitaxel was added to a proper amount of PEG-400, dissolved by shearing at 85° C., and diluted with PEG-400 to 100 ml. Citric acid was added to adjust pH value to 2.84 and 0.2 g activated carbon for injection was added to perform adsorption at 25° C. for 30 min. Next, the solution was filtrated by micro-porous filter membrane, separately packaged, cap-sealed and sterilized by a rotary high-pressure steam sterilizer at 115° C. for 30 min, and the paclitaxel solution was thus obtained;

b) Preparation of the emulsion: 100 g caprylic capric triglyceride for injection and 100 g soybean oil were mixed, heated to 70° C. in water bath, into which 20 g soybean phospholipid for injection was added, dissolved by shearing and stirred well to obtain the oil phase; 22.5 g glycerol was added into 750 ml water for injection, dissolved by stirring and heated to 70° C. to obtain the water phase; the oil phase was mixed with the water phase at 70° C., and followed by emulsification using a shear emulsifying machine for 15 min at a rotation speed of 15000 rpm to obtain a primary emulsion. The primary emulsion was further emulsified by a high-pressure homogenizer under a pressure of 15000 psi. The emulsion was diluted to 1000 ml with water for injection, and its pH value was adjusted to 8.10 by sodium hydroxide solution. The emulsion was filtrated by micro-porous filter membrane, separately packaged, charged with nitrogen, cap-sealed and sterilized by a rotary high-pressure steam sterilizer at 121° C. for 15 min to obtain the emulsion. The average particle size of the emulsion micro-particles was measured to be 240 nm with the pH value of 7.68.

Afore-obtained paclitaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:25 by volume to perform intravenous drip directly.

EXAMPLE 12

Docetaxel Intravenous Infusion Preparation and a Kit Thereof a) Preparation of the pharmaceutical solution: 2.5 g docetaxel was added to a proper amount of PEG-400, dissolved by stirring at 70° C., and diluted with PEG-400 to 100 ml. Citric acid was added to adjust pH value to 3.14, and 0.5 g activated carbon for injection was added to perform adsorption at 25° C. for 60 min. Next, the solution was filtrated by a capsule filter, separately packaged, cap-sealed and sterilized by a rotary high-pressure steam sterilizer at 121° C. for 15 min, and the docetaxel solution was thus obtained;

b) Preparation of the emulsion: 50 g caprylic capric triglyceride for injection and 50 g soybean oil were mixed, heated to 70° C. in water bath, into which 12 g soybean phospholipid for injection was added, dissolved by shearing and stirred well to obtain the oil phase; 22.5 g glycerol was added into 780 ml water for injection, dissolved by stirring and heated to 75° C. to obtain the water phase; the oil phase was mixed with the water phase at 75° C., and followed by emulsification using a shear emulsifying machine for 10 min at a rotation speed of 12000 rpm to obtain a primary emulsion. The primary emulsion was further emulsified by a high-pressure homogenizer under a pressure of 15000 psi. The emulsion was diluted to 1000 ml with water for injection, and its pH value was adjusted to 8.80 by sodium hydroxide solution. The emulsion was filtrated by micro-porous filter membrane, separately packaged, charged with nitrogen, cap-sealed and sterilized by a rotary high-pressure steam sterilizer at 115° C. for 30 min to obtain the emulsion. The average particle size of the emulsion micro-particles was measured to be 210 nm with the pH value of 8.17.

Afore-obtained docetaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:20 by volume to perform intravenous drip directly.

EXAMPLE 13

Paclitaxel Intravenous Infusion Preparation and a Kit Thereof a) Preparation of the pharmaceutical solution: 2.5 g paclitaxel was added to a proper amount of PEG-400, heated to 90° C. to dissolve by shearing, and diluted with PEG-400 to 100 ml. Acetic acid was added to adjust pH value to 3.40, and 0.1 g activated carbon for injection was added to perform adsorption at 60° C. for 15 min. Next, the solution was filtrated by a capsule filter, separately packaged, cap-sealed and sterilized by a rotary high-pressure steam sterilizer at 121° C. for 15 min, and the paclitaxel solution was thus obtained;

b) Preparation of the emulsion: 150 g caprylic capric triglyceride for injection and 150 g soybean oil were mixed, heated to 70° C. in water bath, into which 12 g yolk phospholipid for injection was added, dissolved by shearing and stirred well to obtain the oil phase; 10 g poloxamer-188 and 22.5 g glycerol were added into 650 ml water for injection, dissolved by stirring and heated to 70° C. to obtain the water phase; the oil phase was mixed with the water phase at 70° C., and followed by emulsification using a shear emulsifying machine for 15 min at a rotation speed of 10000 rpm to obtain a primary emulsion. The primary emulsion was further emulsified by a high-pressure homogenizer under a pressure of 20000 psi. The emulsion was diluted to 1000 ml with water for injection, and its pH value adjusted to 6.67 by sodium hydroxide solution. The emulsion was filtrated by a capsule filter, separately packaged, charged with nitrogen, cap-sealed and sterilized by a rotary high-pressure steam sterilizer at 121° C. for 12 min to obtain the emulsion. The average particle size of the emulsion micro-particles was measured to be 340 nm with the pH value of 6.41.

Afore-obtained paclitaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:50 by volume to perform intravenous drip directly.

EXAMPLE 14

Docetaxel Intravenous Infusion Preparation and Kit Thereof a) Preparation of the pharmaceutical solution: 4.0 g docetaxel was added to a proper amount of PEG-400, heated to 85° C. to dissolve by shearing, and diluted with PEG-400 to 100 ml. Citric acid was added to adjust pH value to 3.94 and then 0.05 g activated carbon for injection was added to perform adsorption at 25° C. for 90 min. Next, the solution was filtrated by a capsule filter, separately packaged, cap-sealed, sterilized by a rotary high-pressure steam sterilizer at 121° C. for 15 min, and the docetaxel solution was thus obtained;

b) Preparation of the emulsion: 200 g soybean oil for injection was heated to 65° C. in water bath, into which 12 g yolk phospholipid for injection was added, dissolved by shearing and stirred well to obtain the oil phase; 22.5 g glycerol were added into 750 ml water for injection, dissolved by stirring and heated to 65° C. to obtain the water phase; the oil phase was mixed with the water phase at 65° C., and followed by emulsification using a shear emulsifying machine for 15 min at a rotation speed of 15000 rpm to obtain a primary emulsion. The primary emulsion was further emulsified by a high-pressure homogenizer under a pressure of 20000 psi. The emulsion was diluted to 1000 ml with water for injection, and its pH value was adjusted to 6.50 by sodium hydroxide solution. The emulsion was filtrated by micro-porous filter membrane, separately packaged, charged with nitrogen, cap-sealed and sterilized by a rotary high-pressure steam sterilizer at 121° C. for 15 min to obtain the emulsion. The average particle size of the emulsion micro-particles was measured to be 207 nm with the pH value of 6.12.

Afore-obtained docetaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:75 by volume to perform intravenous drip directly.

EXAMPLE 15

Paclitaxel Intravenous Infusion Preparation and a Kit Thereof a) Preparation of the pharmaceutical solution: 5.0 g paclitaxel was added to a proper amount of PEG-400, dissolved by shearing at 70° C., and diluted with PEG-400 to 100 ml. Malic acid was added to adjust pH value to 3.50, and 1 g activated carbon for injection was added to perform adsorption at 25° C. for 30 min. Next, the solution was filtrated by micro-porous filter membrane, separately packaged, cap-sealed and sterilized by circulating vapor at 100° C. for 45 min, and the paclitaxel solution was thus obtained;

b) Preparation of the emulsion: 100 g caprylic capric triglyceride for injection and 100 g soybean oil were mixed, heated to 70° C. in water bath, into which 20 g soybean phospholipid for injection was added, dissolved by shearing and stirred well to obtain the oil phase; 10 g poloxamer-188 and 22.5 g glycerol were added into 750 ml water for injection, dissolved by stirring and heated to 70° C. to obtain the water phase; the oil phase was mixed with the water phase at 70° C., and followed by emulsification using a shear emulsifying machine for 20 min at a rotation speed of 10000 rpm to obtain a primary emulsion. The primary emulsion was further emulsified by a high-pressure homogenizer under a pressure of 15000 psi. The emulsion was diluted to 1000 ml with water for injection, and its pH value adjusted to 7.40 by sodium hydroxide solution. The emulsion was filtrated by micro-porous filter membrane, separately packaged, charged with nitrogen, cap-sealed and sterilized by a rotary high-pressure steam sterilizer at 121° C. for 15 min to obtain the emulsion. The average particle size of the emulsion micro-particles was measured to be 150 nm with the pH value of 6.84.

Afore-obtained docetaxel solution and medicinal emulsion were respectively loaded in plastic or glass bottles, which were packaged up in a ratio of 1:1 in a same large vessel.

When used, the pharmaceutical solution can be added and evenly dispersed in the emulsion in a ratio of 1:50 by volume to perform intravenous drip directly.

EXAMPLE 16

Paclitaxel Intravenous Infusion Preparation a) Preparation of the pharmaceutical solution: 2.5 g paclitaxel was added to a proper amount of PEG-400, heated to 85° C. to dissolve by shearing, and diluted with PEG-400 to 100 ml. Citric acid was added to adjust pH value to 3.20 and then 0.2 g activated carbon for injection added to perform adsorption at 25° C. for 30 min. Next, the solution was filtrated by micro-porous filter membrane, separately packaged, cap-sealed and sterilized by a rotary high-pressure steam sterilizer at 121° C. for 15 min, and the paclitaxel solution was thus obtained;

b) Commercially available emulsion: specification: 100 ml, 20% medium/long chain fat emulsion; batch No.:

GM0809034; manufacturer: Guangzhou Baxter-Qiaoguang Pharmaceutical Inc.

When used, the pharmaceutical solution can be added and evenly dispersed in the commercially available emulsion in a ratio of 1:25 by volume to perform intravenous drip directly.

EXAMPLE 17

Paclitaxel Intravenous Infusion Preparation a) Preparation of the pharmaceutical solution: 4.0 g paclitaxel was added to a proper amount of PEG-400, dissolved by shearing at 85° C., and diluted with PEG-400 to 100 ml. Citric acid was added to adjust pH value to 3.20 and then 0.15 g activated carbon for injection was added to perform adsorption at 25° C. for 45 min. Next, the solution was filtrated by a capsule filter, separately packaged, cap-sealed and sterilized by a rotary high-pressure steam sterilizer at 121° C. for 15 min, and the paclitaxel solution was thus obtained;
b) Commercially available emulsion: specification: 100 ml, 20% medium/long chain fat emulsion; batch No.: GM0809034; manufacturer: Guangzhou Baxter-Qiaoguang Pharmaceutical Inc.

When used, the pharmaceutical solution can be added and evenly dispersed in the commercially available emulsion in a ratio of 1:40 by volume to perform intravenous drip directly.

EXAMPLE 18

Paclitaxel Intravenous Infusion Preparation a) Preparation of the pharmaceutical solution: 2.5 g paclitaxel was added to a proper amount of PEG-400, dissolved by shearing at 70° C., and diluted with PEG-400 to 100 ml. Citric acid was added to adjust pH value to 3.45 and then 0.2 g activated carbon for injection was added to perform adsorption at 25° C. for 30 min. Next, the solution was filtrated by micro-porous filter membrane, separately packaged, cap-sealed and sterilized by a rotary high-pressure steam sterilizer at 121° C. for 30 min, and the paclitaxel solution was thus obtained;
b) Commercially available emulsion: specification: 250 ml, 20% medium/long chain fat emulsion; batch No.: 80BM072; manufacturer: Huarui pharmaceutical Inc.

When used, the pharmaceutical solution can be added and evenly dispersed in the commercially available emulsion in a ratio of 1:15 by volume to perform intravenous drip directly.

EXAMPLE 19

Paclitaxel Intravenous Infusion Preparation a) Preparation of the pharmaceutical solution: 4.0 g paclitaxel was added to a proper amount of PEG-400, dissolved by shearing at 90° C., and diluted with PEG-400 to 100 ml. Hydrochloric acid was added to adjust pH value to 3.04 and then 0.5 g activated carbon for injection was added to perform adsorption at 60° C. for 15 min. Next, the solution was filtrated by a capsule filter, separately packaged, cap-sealed and sterilized by a rotary high-pressure steam sterilizer at 121° C. for 15 min, and the paclitaxel solution was thus obtained;
b) Commercially available emulsion: specification: 250 ml, 20% medium/long chain fat emulsion; batch No.: F090203C2; manufacturer: Sichuan Kelun Pharmaceutical Joint Stock Company.

When used, the pharmaceutical solution can be added and evenly dispersed in the commercially available emulsion in a ratio of 1:60 by volume to perform intravenous drip directly.

EXAMPLE 20

Paclitaxel Intravenous Infusion Preparation a) Preparation of the pharmaceutical solution: 2.5 g paclitaxel was added to a proper amount of PEG-400, dissolved by shearing at 85° C., and diluted with PEG-400 to 100 ml. Citric acid was added to adjust pH value to 3.24 and then 0.2 g activated carbon for injection was added to perform adsorption at 25° C. for 30 min. Next, the solution was filtrated by micro-porous filter membrane, separately packaged, cap-sealed and sterilized by a rotary high-pressure steam sterilizer at 121° C. for 30 min, and the paclitaxel solution was thus obtained;
b) Commercially available emulsion: specification: 250 ml, 20% medium/long chain fat emulsion; batch No.: F090203C2; manufacturer: Sichuan Kelun Pharmaceutical Joint Stock Company.

When used, the pharmaceutical solution can be added and evenly dispersed in the commercially available emulsion in a ratio of 1:25 by volume to perform intravenous drip directly.

EXAMPLE 21

Paclitaxel Intravenous Infusion Preparation a) Preparation of the pharmaceutical solution: 2.5 g paclitaxel was added to a proper amount of PEG-400, dissolved by shearing at 70° C., and diluted with PEG-400 to 100 ml. Citric acid was added to adjust pH value to 3.24 and then 0.2 g activated carbon for injection was added to perform adsorption at 25° C. for 30 min. Next, the solution was filtrated by micro-porous filter membrane, separately packaged, cap-sealed and sterilized by a rotary high-pressure steam sterilizer at 121° C. for 30 min, and the paclitaxel solution was thus obtained;
b) Commercially available emulsion: specification: 250 ml, 20% long chain fat emulsion; batch No.: 0811212-1; manufacturer: Zhejiang Kanglaite Pharmaceutical Inc.

When used, the pharmaceutical solution can be added and evenly dispersed in the commercially available emulsion in a ratio of 1:25 by volume to perform intravenous drip directly.

EXAMPLE 22

Paclitaxel Intravenous Infusion Preparation a) Preparation of the pharmaceutical solution: 6.0 g paclitaxel was added to a proper amount of PEG-400, dissolved by shearing at 70° C., and diluted with PEG-400 to 100 ml. Citric acid was added to adjust pH value to 3.24 and then 0.2 g activated carbon for injection was added to perform adsorption at 25° C. for 30 min. Next, the solution was filtrated by micro-porous filter membrane, separately packaged, cap-sealed and sterilized by a rotary high-pressure steam sterilizer at 121° C. for 30 min, and the paclitaxel solution was thus obtained;
b) Commercially available emulsion: specification: 250 ml, 20% medium/long chain fat emulsion; batch No.: 8192A181; manufacturer: Beilang Pharmaceutical Inc, Germany.

When used, the pharmaceutical solution can be added and evenly dispersed in the commercially available emulsion in a ratio of 1:80 by volume to perform intravenous drip directly.

EXAMPLE 23

Paclitaxel Intravenous Infusion Preparation a) Preparation of the pharmaceutical solution: 2.5 g paclitaxel was added to a proper amount of PEG-400, dissolved by shearing at 70° C., and diluted with PEG-400 to 100 ml. Citric acid was added to adjust pH value to 3.24 and then 0.2 g activated carbon for injection was added to perform adsorption at 25° C. for 30 min. Next, the solution was filtrated by micro-porous filter membrane, separately packaged, cap-sealed and sterilized by a rotary high-pressure steam sterilizer at 115° C. for 30 min, and the paclitaxel solution was thus obtained;
b) Commercially available emulsion: specification: 250 ml, 20% medium/long chain fat emulsion; batch No.: GM0810022; manufacturer: Guangzhou Baxter-Qiaoguang Pharmaceutical Inc.

When used, the pharmaceutical solution can be added and evenly dispersed in the commercially available emulsion in a ratio of 1:25 by volume to perform intravenous drip directly.

EXAMPLE 24

Paclitaxel Intravenous Infusion Preparation a) Preparation of the pharmaceutical solution: 2.5 g paclitaxel was added to a proper amount of PEG-400, dissolved by shearing at 70° C., and diluted with PEG-400 to 100 ml. Citric acid was added to adjust pH value to 3.32 and then 0.2 g activated carbon for injection was added to perform adsorption at 25° C. for 30 min. Next, the solution was filtrated by micro-porous filter membrane, separately packaged, cap-sealed and sterilized by a rotary high-pressure steam sterilizer at 121° C. for 15 min, and the paclitaxel solution was thus obtained;
b) Commercially available emulsion: specification: 250 ml, 30% long chain fat emulsion; batch No.: GM0810022; manufacturer: Huarui pharmaceutical Inc.

When used, the pharmaceutical solution can be added and evenly dispersed in the commercially available emulsion in a ratio of 1:25 by volume to perform intravenous drip directly.

EXAMPLE 25

Docetaxel Intravenous Infusion Preparation a) Preparation of the pharmaceutical solution: 2.5 g docetaxel was added to a proper amount of PEG-400, dissolved by shearing at 95° C., and diluted with PEG-400 to 100 ml. Citric acid was added to adjust pH value to 3.40 and then 0.2 g activated carbon for injection was added to perform adsorption at 25° C. for 30 min. Next, the solution was filtrated by micro-porous filter membrane, separately packaged, cap-sealed and sterilized by a rotary high-pressure steam sterilizer at 121° C. for 15 min, and the docetaxel solution was thus obtained;
b) Commercially available emulsion: specification: 100 ml, 20% medium/long chain fat emulsion; batch No.: GM0809034; manufacturer: Guangzhou Baxter-Qiaoguang Pharmaceutical Inc.

When used, the pharmaceutical solution can be added and evenly dispersed in the commercially available emulsion in a ratio of 1:25 by volume to perform intravenous drip directly.

EXAMPLE 26

Docetaxel Intravenous Infusion Preparation a) Preparation of the pharmaceutical solution: 2.5 g docetaxel was added to a proper amount of PEG-400, dissolved by shearing at 60° C., and diluted with PEG-400 to 100 ml. Citric acid was added to adjust pH value to 3.32 and then 0.2 g activated carbon for injection was added to perform adsorption at 25° C. for 30 min. Next, the solution was filtrated by micro-porous filter membrane, separately packaged, cap-sealed and sterilized by a rotary high-pressure steam sterilizer at 121° C. for 15 min, and the docetaxel solution was thus obtained;
b) Commercially available emulsion: specification: 250 ml, 30% long chain fat emulsion; batch No.: GM0810022; manufacturer: Huarui pharmaceutical Inc.

When used, the pharmaceutical solution can be added and evenly dispersed in the commercially available emulsion in a ratio of 1:25 by volume to perform intravenous drip directly.

EXAMPLE 27

Paclitaxel Intravenous Infusion Preparation a) Preparation of the pharmaceutical solution: 5.0 g paclitaxel was added to a proper amount of PEG-400, dissolved by shearing at 95° C., and diluted with PEG-400 to 100 ml. Citric acid was added to adjust pH value to 3.5 and then 0.2 g activated carbon for injection was added to perform adsorption at 25° C. for 30 min. Next, the solution was filtrated by 0.22 μm micro-porous filter membrane to sterilize, separately packaged and cap-sealed, and the paclitaxel solution was thus obtained;
b) Commercially available emulsion: specification: 100 ml, 20% medium/long chain fat emulsion; batch No.: GM0809034; manufacturer: Guangzhou Baxter-Qiaoguang Pharmaceutical Inc.

When used, the pharmaceutical solution can be added and evenly dispersed in the commercially available emulsion in a ratio of 1:50 by volume to perform intravenous drip directly.

EXAMPLE 28

Paclitaxel Intravenous Infusion Preparation a) Preparation of the pharmaceutical solution: 5.0 g paclitaxel was added to a proper amount of PEG-400, dissolved by shearing at 80° C., and diluted with PEG-400 to 100 ml. Lactic acid was added to adjust pH value to 3.28 and then 0.2 g activated carbon for injection was added to perform adsorption at 30° C. for 45 min. Next, the solution was filtrated by 0.22 μm micro-porous filter membrane to sterilize, separately packaged and cap-sealed, and the paclitaxel solution was thus obtained;
b) Commercially available emulsion: specification: 100 ml, 20% medium/long chain fat emulsion; batch No.: GM0809034; manufacturer: Guangzhou Baxter-Qiaoguang Pharmaceutical Inc.

When used, the pharmaceutical solution can be added and evenly dispersed in the commercially available emulsion in a ratio of 1:70 by volume to perform intravenous drip directly.

The invention claimed is:

1. A pharmaceutical solution of taxanes consisting of a taxane, a pH regulator, a solvent and optional pharmaceutical adjuvant, wherein amounts of ingredients are as follows:

taxanes 1~8% (g/ml)

pH of the pharmaceutical solution of taxanes is 2.0~4.0 the balance is a solvent and optional pharmaceutical adjuvant, wherein the pharmaceutical adjuvants are selected from isotonic regulator and chelating agent.

2. The pharmaceutical solution of taxanes of claim 1, wherein amounts of ingredients are as follows:

taxanes 1~6% (g/ml)

pH of the pharmaceutical solution of taxanes is 2.0~3.98 the balance is a solvent and optional pharmaceutical adjuvant.

3. The pharmaceutical solution of taxanes of claim 2, wherein the pH of the pharmaceutical solution of taxanes is 3~3.98.

4. The pharmaceutical solution of taxanes of claim 1, wherein the taxane is paclitaxel or docetaxel.

5. The pharmaceutical solution of taxanes of claim 1, wherein the pH regulator is a water-soluble acid.

6. The pharmaceutical solution of taxanes of claim 5, wherein the water-soluble acid includes one or more acids selected from the group consisting of citric acid, lactic acid, malic acid, hydrochloric acid, acetic acid, phosphoric acid and tartaric acid.

7. The pharmaceutical solution of claim 6, wherein the water-soluble acid is citric acid.

8. The pharmaceutical solution of taxanes of claim 1, wherein the solvent includes one or more solvents selected from the group consisting of PEG-200, PEG-300, PEG-400, PEG-600, propylene glycol, glycerol, anhydrous ethanol and water for injection.

9. The pharmaceutical solution of claim 8, wherein the solvent is PEG-400.

10. A method for preparing a pharmaceutical solution of taxanes of claim 1, wherein the method includes steps of dissolving the taxanes and the pH regulator in the solvent; additional pharmaceutical adjuvants are added, if necessary.

11. The preparation method of claim 10, wherein the method includes following steps: weighing paclitaxel or docetaxel; adding paclitaxel or docetaxel into a solvent; dissolved by heating and stirring at 50~100° C. or by shearing; diluting the mixture with the solvent; adjusting pH to 2.0~4.0 with the pH regulator; adding 0.01%~3% (g/ml) activated carbon for injection to perform adsorption by heating at 25~100° C. for 15~120 min; then filtering, separately packaging, cap-sealing and sterilizing to obtain the pharmaceutical solution of taxanes.

12. A kit comprising the pharmaceutical solution of taxanes according to claim 1 and an emulsion, wherein the pharmaceutical solution of taxanes and the emulsion are loaded in two separate vessels that are arranged in a combined manner.

* * * * *